US008628969B2

(12) United States Patent
Kasajima

(10) Patent No.: US 8,628,969 B2
(45) Date of Patent: Jan. 14, 2014

(54) METHOD FOR QUANTIFICATION OF CAROTENOID

(75) Inventor: Naoki Kasajima, Mishima-gun (JP)

(73) Assignee: Suntory Beverage & Food Limited, Tokyo (JP)

(*) Notice: Subject to any disclaimer, the term of this patent is extended or adjusted under 35 U.S.C. 154(b) by 0 days.

(21) Appl. No.: 13/505,067

(22) PCT Filed: Oct. 15, 2010

(86) PCT No.: PCT/JP2010/068113
§ 371 (c)(1),
(2), (4) Date: Apr. 30, 2012

(87) PCT Pub. No.: WO2011/074317
PCT Pub. Date: Jun. 23, 2011

(65) Prior Publication Data
US 2012/0214244 A1 Aug. 23, 2012

(30) Foreign Application Priority Data
Dec. 15, 2009 (JP) ................. 2009-283734

(51) Int. Cl.
*G01N 30/02* (2006.01)
*G01N 30/00* (2006.01)
(52) U.S. Cl.
USPC ............. 436/20; 436/131; 435/7.1; 424/9.1
(58) Field of Classification Search
USPC .......... 436/20, 131; 435/7.1; 424/9.1
See application file for complete search history.

(56) References Cited

U.S. PATENT DOCUMENTS

2005/0074404 A1* 4/2005 Aleo .............................. 424/9.1

FOREIGN PATENT DOCUMENTS

JP    6-94700    4/1994

OTHER PUBLICATIONS

Takashi Sumida et al., "Quantitative Analysis of β-*Cryptoxanthin* in Satsuma Mandarin (*Citrus unshiu* Marc.) Juice by $C_{30}$ Stationary Phase High Performance Liquid Chromatography," Journal of the Japanese Society for Food Science and Technology, Jul. 15, 1999, vol. 46, No. 7, pp. 467-472, including excerpted English translation.
Hiroshi Nakamura, "Eki Kuro Ryu no Maki," Nov. 30, 2002, p. 102, including excerpted English translation.
International Search Report mailed Jan. 18, 2011 in PCT/JP2010/068113 filed Oct. 15, 2010.

(Continued)

*Primary Examiner* — Krishnan S Menon
*Assistant Examiner* — Rebecca M Fritchman
(74) *Attorney, Agent, or Firm* — Drinker Biddle & Reath LLP

(57) ABSTRACT

Provided is a method for quantitative analysis of carotenoids such as β-cryptoxanthin contained in a sample such as citrus fruit or the like which enables simple and accurate quantitative analysis.
An internal standard such as lycopene or retinal is used, whereby work is facilitated and an error of a measured value is reduced. Further, a dehydrating agent is added during saponification reaction in the preparation of a sample for analysis, whereby a deviation of a measured value can be reduced.

11 Claims, 2 Drawing Sheets

(56) References Cited

OTHER PUBLICATIONS

Chinese Office Action issued May 28, 2013, in Chinese Patent Application No. 20108011299.0.

Cortés et al., "Identification and Quantification of Carotenoids Including Geometrical Isomers in Fruit and Vegetable Juices by Liquid Chromatography with Ultraviolet-Diode Array Detection," Journal of Agriculture and Food Chemistry, 2004, 52, 2203-2212.

Wang et al., "Preliminary Identification of Red Carotenoids from *Potamogeton crispus L.*" Scientia Agricuitura Sinica, 2004, 37(9), 1363-1368.

* cited by examiner

METHOD FOR QUANTIFICATION OF CAROTENOID

CROSS REFERENCE TO RELATED APPLICATIONS

This application is the National Stage of International Application No. PCT/JP2010/068113, filed Oct. 15, 2010, and claims benefit of Japanese Application No. 2009-283734, filed Dec. 15, 2009, all of which are herein incorporated by reference in their entirety.

TECHNICAL FIELD

The present invention relates to a method for quantitative analysis of carotenoids. In particular, the present invention relates to a method for quantitative analysis of carotenoids contained in a citrus fruit, a beverage containing fruit juice, etc.

BACKGROUND ART

Carotenoid is a pigment which is widely distributed in the animal and plant kingdoms, and is classified as tetraterpene ($C_{40}$) having isoprene $C_5H_8$ as a structural unit. Examples of carotenoids include α-carotene, β-carotene, γ-carotene, lycopene, cryptoxanthin, lutein, zeaxanthin, canthaxanthin, fucoxanthin, antheraxanthin, violaxanthin and the like. Carotenoids include a substance which may be converted within the animal body to vitamin A (provitamin A), and a substance having high anti-oxidant action is also known.

Among these carotenoids, β-cryptoxanthin contained in citrus fruits, such as Satsuma mandarin (*Citrus unshiu* Marc.) and Valencia orange, loquat, persimmon, peach, red bell pepper, papaya and the like clearly has not only characteristics as provitamin A but also high anticarcinogenic action and high anti-oxidant action. Hence, β-cryptoxanthin has drawn great attention in recent years.

β-Cryptoxanthin tends to be affected by light, heat and oxygen; β-cryptoxanthin tends to be isomerized (converted into a cis isomer) by light and heat and, furthermore, polyene is cleaved by oxidation. There have been only few studies on a method for the easy and accurate measurement of the amount of β-cryptoxanthin contained in fruit juice or the like.

Non-patent Document 1 describes a method of quantitatively determining β-cryptoxanthin contained in Satsuma mandarin juice. Specifically, in the method described in Non-patent Document 1, first 1 g of diatomaceous earth and 10 ml of ethanol are added to 10 g of fruit juice and stirred, and then the mixture is poured onto a thin bed of diatomaceous earth on a glass filter, and washed with ethanol until the color of residues disappears, whereby an ethanol extract is obtained. This ethanol extract (about 60 ml) is then transferred by washing to a separatory funnel. Then, equivalent amounts of ether and distilled water are added, and a gas layer is replaced with nitrogen gas, followed by shaking to distribute carotenoid to the ether. This ether solution is concentrated in vacuo, and an equivalent amount of 10% methanolic KOH solution is added. The mixture is allowed to stand at 20° C. in a dark place under a nitrogen atmosphere for 1 hour to conduct saponification treatment. An unsaponifiable material is fractionated with ether from the solution having been subjected to the saponification treatment, and is washed with distilled water until an alkali is removed. This is followed by dehydration with anhydrous sodium sulfate and removal of the solvent by distillation in vacuo under a nitrogen atmosphere. Thereafter, a mobile phase solvent is added to give a volume of 10 ml, and a solution having been passed through a 0.45-μm membrane filter is analyzed by an HPLC apparatus equipped with a $C_{30}$ analysis column. A calibration curve is formed using a sample prepared similarly using a β-cryptoxanthin standard specimen, and quantitative analysis of β-cryptoxanthin in the fruit juice is conducted.

CITATION LIST

Non-Patent Document

Non-patent Document 1: Takashi Sumida and four other coauthors, "Quantitative Analysis of β-Cryptoxanthin in Satsuma Mandarin (*Citrus unshiu* Marc.) Juice by using $C_{30}$ Stationary Phase High Performance Liquid Chromatography," Journal of the Japanese Society for Food Science and Technology, July 1999, Vol. 46, No. 7, p. 467-472

SUMMARY OF INVENTION

Technical Problem

The method described in Non-patent Document 1 is a method of measuring the total amount of β-cryptoxanthin

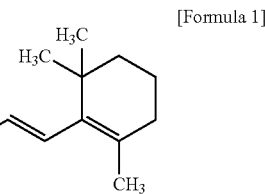

[Formula 1]

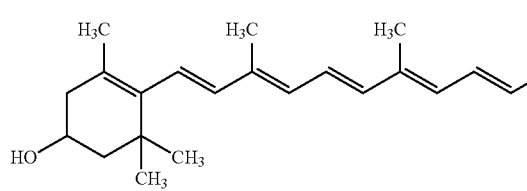

β-Cryptoxanthin contained in initially-weighed Satsuma mandarin juice. If, for example, a sample remains in an original vessel when it is transferred from the original vessel to another vessel, this may cause an error. In such a case, in general an attempt is made to recover the whole amount of β-cryptoxanthin by repeating washing, but this results in an increase in the volume of the sample, causing problems that it takes time to concentrate, etc. In the method described in Non-patent Document 1, ether and distilled water are added in the same amounts as that of ethanol used to wash residues on the glass filter, and thereafter the ether solution is concentrated under reduced pressure. Hence, when a large amount of ethanol is used in washing, the amount of ether at the time of concentration is large; thus, it takes time to concentrate. Further, since ether may cause bumping or catch fire, close attention is always required during the operation, requiring a lot of work. Further, when the operation time is long, β-cryptoxanthin which is an object to be measured is affected by light and oxygen and thereby deteriorated. This may lead to another error.

An object of the present invention is to provide a method for quantitative analysis which overcomes the above disadvantages of the conventional method and enables simple and more accurate quantitative analysis.

Solution to Problem

The present inventor found that by adding an internal standard substance to a sample such as fruit juice, the amount of a solvent used, the time, work and costs required to conduct the concentration operation, and an error of a measured value can be reduced. Further, the present inventor studied the type of an internal standard substance used at that time. The present inventor also found that by adding a dehydrating agent prior to saponification reaction, a deviation of a measured value can be reduced. By these findings, the present invention was completed.

Specifically, the present invention relates to:
1. A method for quantitative analysis of β-cryptoxanthin contained in a sample, comprising: mixing the specimen with a diethyl ether solution containing an internal standard substance selected from the group consisting of lycopene and retinal; obtaining a diethyl ether layer; adding a dehydrating agent to the obtained diethyl ether layer to dehydrate the diethyl ether layer; after the dehydration, adding an alkali solution to conduct saponification reaction; after the reaction, adding an acid, allowing the mixture to stand still, and then obtaining a diethyl ether layer; and subjecting the diethyl ether layer to high-performance liquid chromatography and conducting quantitative analysis of β-cryptoxanthin using an internal standard method;
2. The method of 1, wherein the internal standard substance is retinal;
3. The method of 1, wherein the dehydrating agent is sodium sulfate;
4. The method of any one of 1 to 3, wherein the specimen is a liquid containing fruit juice or vegetable juice;
5. The method of 4, wherein the liquid containing fruit juice or vegetable juice is a liquid containing citrus fruit juice;
6. The method of 4, wherein the liquid containing fruit juice or vegetable juice is a beverage containing fruit juice; and
7. The method of any one of 1 to 6, wherein the saponification reaction is conducted at 5 to 60° C. in a dark place for 1 to 3 hours.

Advantageous Effect of Invention

In the method of the present invention, if a sample and an internal standard substance are accurately weighed at the beginning, the level of accuracy required in a subsequent operation is not so high. Thus, the operation is relatively easy even for an unskilled person. Further, since a large amount of solvent is not used in washing, the cost of solvent can be reduced, and no operation of concentration is required. Furthermore, since the sample preparation time is reduced, an error caused by a structural change of an object to be measured can be reduced. Further, a deviation of a measured value can be reduced by a simple operation.

DESCRIPTION OF EMBODIMENT

Figure 1:
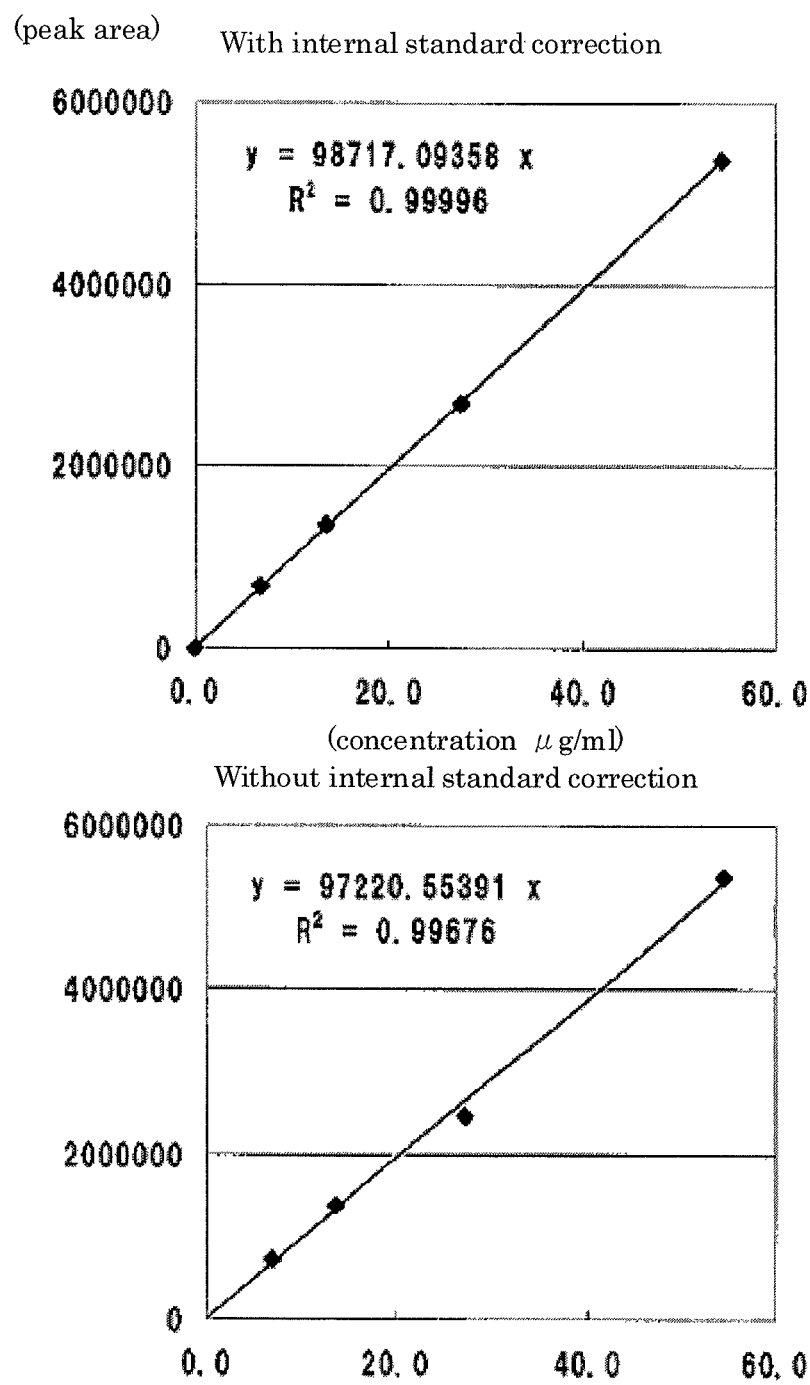
FIG. 1 shows a comparison of a calibration curve in a case of using an internal standard with a calibration curve in a case of using no internal standard.

In a method of the present invention, a sample such as fruit juice is mixed with an organic solvent solution containing an internal standard substance, and an organic solvent layer is taken, followed by addition of a dehydrating agent to the organic solvent layer to dehydrate the organic solvent layer. After the organic solvent layer is dehydrate, an alkali solution is added to conduct saponification reaction. Then, adding an acid, and the mixture is allowed to stand still, followed by subjecting the organic solvent layer to high-performance liquid chromatography (HPLC) and conducting quantitative analysis.

The method of the present invention is suitable especially for quantitative analysis of β-cryptoxanthin, but is also applicable to quantitative analysis of carotenoids other than (β-cryptoxanthin.

(Sample)

By the method of the present invention, carotenoids contained in a sample such as a fruit juice, vegetable juice and beverage can be analyzed quantitatively. Particularly, a juice of fruit containing a large amount of β-cryptoxanthin, in particular a citrus fruit juice, or a liquid containing fruit juice can preferably be used as a sample. Examples of a fruit containing a large amount of β-cryptoxanthin include citrus fruits such as Satsuma mandarin and Valencia orange, loquat, persimmon, peach and papaya. The sample may be a juice of vegetable such as red bell pepper. Such a fruit or vegetable is appropriately washed, and juice of the fruit or vegetable is extracted using a commonly-used juice extractor such as an in-line juice extractor, a chopper pulper juice extractor and a Brown juice extractor and, as necessary, subjected to filtration treatment and the like so that the resulting juice can be used as a fruit or vegetable juice sample.

A beverage containing fruit or vegetable juice which is prepared by adding a commonly-used additive(s) and the like to a liquid containing fruit or vegetable juice, or a beverage to which β-cryptoxanthin is externally added may also be used as a sample. These beverages may contain water, alcohol, carbon dioxide gas and the like, and also an additive such as a sweetening agent, coloring agent, thickening agent, stabilizing agent, antioxidant, flavoring agent, acidulant, food preservative, gelling agent, paste agent, emulsifying agent and pH adjusting agent.

A solid food such as jelly can also be used as a sample in the present invention if it is liquefied by a known method.

When a sample has high viscosity or Brix (sugar content) and is thus not suitable for preparation of a sample for HPLC analysis, the sample may appropriately be diluted by a commonly-used method.

(Mixing Standard Solution with Sample)

In the method of the present invention, first, an accurately-weighed sample is mixed with an accurately-weighed organic solvent solution (standard solution) containing an internal standard substance. The accurate weighing can be conducted easily by use of a whole pipette (volumetric pipette, Vollpipette) or the like.

As an organic solvent, diethyl ether, petroleum ether, n-hexane, cyclohexane, chloroform, ethyl acetate or the like can be used. Among these, diethyl ether is preferred in terms of extraction efficiency.

As an internal standard substance to be added to a standard solution, it is preferable to use a substance which is not appeared in a sample (e.g., fruit juice), is stable during preparation of a sample for analysis, has elution behavior, physical properties, characteristics and the like which are not significantly different from those of a substance to be measured (e.g., β-cryptoxanthin), is soluble in a mobile phase of HPLC, and can be separated completely by HPLC from the substance to be measured. Internal standard substances which are inexpensive and easily available are also preferred. Specific examples include lycopene, retinal, retinol, dehydroretinol, α-carotene, β-carotene, capsaicin, astaxanthin and fucoxanthin. Among these, lycopene or retinal is preferred. Retinal is particularly preferred. Since retinal has a short retention time in HPLC measurement, the measurement time can be reduced. Furthermore, since the peak of retinal is sharper than that of lycopene, an error in calculation of a peak area decreases and, thus, a deviation and an error of a measured value can be reduced. Further, retinal is available at low cost, compared with lycopene.

A standard solution can be prepared by accurately weighing an internal standard substance, adding an organic solvent (e.g., diethyl ether) and dissolving it well under ultrasonic wave or the like, and adding the residual solvent to a predetermined volume. The concentration of an internal standard substance in a standard solution is not particularly limited. In general, the concentration is about 1 to 100 μg/ml, preferably about 20 to 40 μg/ml.

The mix ratio of the sample to the standard solution may appropriately be determined according to the type of the sample and the like such that the internal standard substance can be detected in the subsequent HPLC measurement. In general, the mix ratio is sample: standard solution=about 1:3 to 1:1 (volume ratio).

Preferably, the mixing of the sample with the standard solution is carried out in an inert atmosphere in order to prevent deterioration by oxidation of a substance to be measured (β-cryptoxanthin, etc.). Specifically, it is preferable to use a vessel equipped with a lid and replace gas in a head space of the vessel with an inert gas such as nitrogen gas.

When the sample is mixed with the standard solution, liquid-liquid distribution occurs, and carotenoid which is an object to be measured transfers to an organic solvent layer (e.g., diethyl ether layer). Then, the organic solvent layer is separated by centrifugal separation (1000 to 5000 rpm, about 3 to 20 minutes) or the like, and a predetermined volume is removed. The organic solvent layer thus removed will be subjected to the subsequent saponification reaction. The amount of organic solvent layer to be subjected to the saponification reaction is not particularly limited. In general, the amount is about 1 to 3 ml.

(Saponification Reaction)

Then, to the organic solvent layer thus obtained, an organic solvent solution of alkali metal hydroxide is added to conduct the saponification reaction. At this time, a dehydrating agent is added to the organic solvent layer prior to the addition of an alkali in the method of the present invention to thereby dehydrate and dry the organic solvent layer. The present inventor found that by adding a dehydrating agent prior to saponification, a deviation of a value measured in the subsequent HPLC can be reduced. As the dehydrating agent, sodium sulfate, magnesium sulfate, molecular sieve or the like can be used. Sodium sulfate is particularly preferred.

The proportion of the dehydrating agent added to the organic solvent layer is not particularly limited, but the dehydrating agent is added in an amount of about 0.025 to 0.25 g, preferably about 0.10 to 0.15 g, with respect to 1 ml of organic solvent layer. The dehydrating agent is added to the organic solvent layer, stirred, and stood still for about 3 to 10 minutes, whereby the organic solvent layer is dehydrated and dried.

After the organic solvent layer is dehydrated, an alkali solution is added to the organic solvent layer to conduct saponification reaction. As to the type of an alkali solution added, any alkali solution which is commonly used in saponification reaction can be used. Examples include methanolic potassium hydroxide, sodium hydroxide, calcium hydroxide and lithium hydroxide.

Although the conditions of saponification reaction are not particularly limited, since β-cryptoxanthin is affected by light and thereby isomerized, it is preferable to conduct the reaction in a dark place. The reaction temperature is not particularly limited. In general, saponification reaction can be conducted at about 5 to 60° C. However, since β-cryptoxanthin tends to be isomerized by heat, it is preferable to conduct the saponification reaction at about room temperature, for example about 15 to 30° C. Further, since (β-cryptoxanthin is decomposed by oxidation, it is preferable to conduct the reaction in an inert atmosphere such as nitrogen gas. Further, since saponification is not sufficiently developed when the reaction time is excessively short, and isomerization and decomposition may occur when the reaction time is excessively long, the reaction time is preferably about 1 to 3 hours, more preferably about 1 to 2 hours, most preferably about 1 hour.

After the saponification reaction, an acid is added and stirred, and then the mixture is stood still to thereby transfer carotenoids which are substances to be measured to the organic solvent layer. Examples of an acid used at this time include hydrochloric acid, sulfuric acid and nitric acid. Thereafter, the organic solvent layer is taken, passed through a commonly-used filter such as a 0.45-μm membrane filter, and subjected to high-performance liquid chromatography (HPLC).

(Quantitative Analysis by HPLC)

Analysis by high-performance liquid chromatography (HPLC) can be performed using a known method which is commonly used in measurement of carotenoids. As a column, a $C_{30}$ column or the like which is commonly used in measurement of carotenoids can be used. Detection can be performed using an ultraviolet absorbance detector. Internal standard correction is performed by a known method using a measured value of the substance to be measured which is obtained and a calibration curve which is prepared separately, whereby the substance to be measured which is contained in the sample can be analyzed quantitatively.

In the present invention, since an internal standard substance is used, accuracy of operation is not so required and, thus, the operation is relatively easy even for an unskilled person. This makes it possible to reduce inaccuracy of a measured value associated with complex operation. Further, the cost of solvent used in washing can be reduced, and the time and cost of equipment and the like required to conduct the concentration can also be reduced. Furthermore, since the time for preparation of a sample for analysis is reduced, a structural change of a substance to be measured such as isomerization and decomposition can be reduced and, thus, an error of a measured value can also be reduced. Further, by adding a dehydrating agent prior to the saponification reaction, a deviation of a measured value can be reduced.

EXAMPLES

The present invention is described in detail by the following Examples. However, it is understood that the scope of the present invention is not limited by the Examples.

[Procedure of Quantitative Analysis of β-Cryptoxanthin]

(Preparation of standard solution containing internal standard substance) Under ultrasonic wave, 2.0 mg of an internal standard substance was dissolved in a small amount of diethyl ether, passed through a filter (0.45 μm, 4 mm (diameter)), and added thereinto diethyl ether to a total volume of the solution being 100 ml.

(Preparation of Sample for HPLC Analysis)

In a test tube equipped with a screw cap, 4.0 ml of a liquid sample and 4.0 ml of the standard solution prepared above were charged, and gas in a head space was replaced with nitrogen gas, followed by closing the cap of the test tube. After liquid-liquid distribution, centrifugal separation was performed at 2000 rpm for 5 minutes. Then, 3.0 ml of a diethyl ether layer was taken and charged in another test tube equipped with a screw cap, and anhydrous sodium sulfate (about 0.5 g) was added to dehydrate the diethyl ether layer. After the diethyl ether layer was dehydrated, 0.5 ml of 10% methanolic potassium hydroxide was added, and gas in a head space was replaced with nitrogen gas, followed by closing the cap of the test tube. Thereafter, the test tube was stood still in a dark place at room temperature for 1 hour. Then, 1.0 ml of 1M hydrochloric acid was added and stirred well with a test tube mixer. After the mixture was stood still for 5 minutes, a diethyl ether layer was passed through a filter (0.45 μm, 4 mm (diameter)) to obtain a sample for HPLC analysis.

(Analysis by HPLC)

HPLC measurement was conducted under the following conditions.

Column: YMC Carotenoid $C_{30}$ (4.6 (diameter)×250 mm, 5 μm, YMC Co., Ltd.)

Detection: 451 nm (β-cryptoxanthin, lycopene), 381 nm (retinal)

Column temperature: 40° C.

Mobile phase A: Methanol was added to 1.0 g of ammonium acetate to obtain a volume of 1000 ml Mobile phase B: Methanol and t-butylmethylether (1:1 mixed solution) were added to 1.0 g of ammonium acetate to obtain a volume of 1000 ml Gradient: mobile phase B 0%-0%-100%-100% (0 min.-2 min.-8 min.-20 min.)

Flow rate: 1.5 ml/min

Injection volume: 10 μl.

(Calculation of β-Cryptoxanthin Concentration)

A β-cryptoxanthin standard substance (Shikoku Yashima Pure Chemicals Co., Ltd.) was dissolved in a standard solution to give a concentration of 5 to 50 μg/ml. Quantitative analysis was conducted three or more times in each concentration to prepare a calibration curve. The concentration of β-cryptoxanthin obtained from the calibration curve was corrected using the following formula.

$$\text{Concentration of β-cryptoxanthin} = \text{Con} \times (At_1/At_2)$$

Con: Concentration of β-cryptoxanthin derived from the calibration curve (μg/ml)

$At_1$: Peak area of internal standard in standard solution $At_2$: Peak area of internal standard in sample for analysis.

Example 1

[Comparison Between Presence and Absence of Internal Standard]

A calibration curve of β-cryptoxanthin which was prepared in accordance with the above method using lycopene as an internal standard was compared with a calibration curve which was prepared without using an internal standard. The results are shown in FIG. 1.

Example 2

[Study of Internal Standard Substance]

In accordance with the procedure of quantitative analysis described above, quantitative analysis of β-cryptoxanthin in 6 kinds of Satsuma mandarin juice beverages (7% of concentrated Satsuma mandarin juice, 0.3% of flavoring agent, 0.02% of antioxidant, 0.01% of coloring agent) was conducted. As an internal standard, lycopene or retinal was used. Each sample was measured three times, and deviations of measured values (standard deviation) were determined. The results are shown in Table 1.

TABLE 1

| | Concentration of β-cryptoxanthin (μg/ml) Internal standard: lycopene | Deviation (STDEV) | Concentration of β-cryptoxanthin (μg/ml) Internal standard: retinal | Deviation (STDEV) |
|---|---|---|---|---|
| Sample 1 | 6.60 | 0.19 | 7.02 | 0.15 |
| Sample 2 | 6.48 | 0.08 | 6.81 | 0.09 |
| Sample 3 | 5.49 | 0.11 | 5.79 | 0.03 |
| Sample 4 | 6.00 | 0.06 | 6.37 | 0.06 |
| Sample 5 | 5.42 | 0.08 | 5.69 | 0.04 |
| Sample 6 | 6.12 | 0.16 | 6.32 | 0.08 |
| Average | 6.02 | 0.11 | 6.33 | 0.08 |

Figure 2:
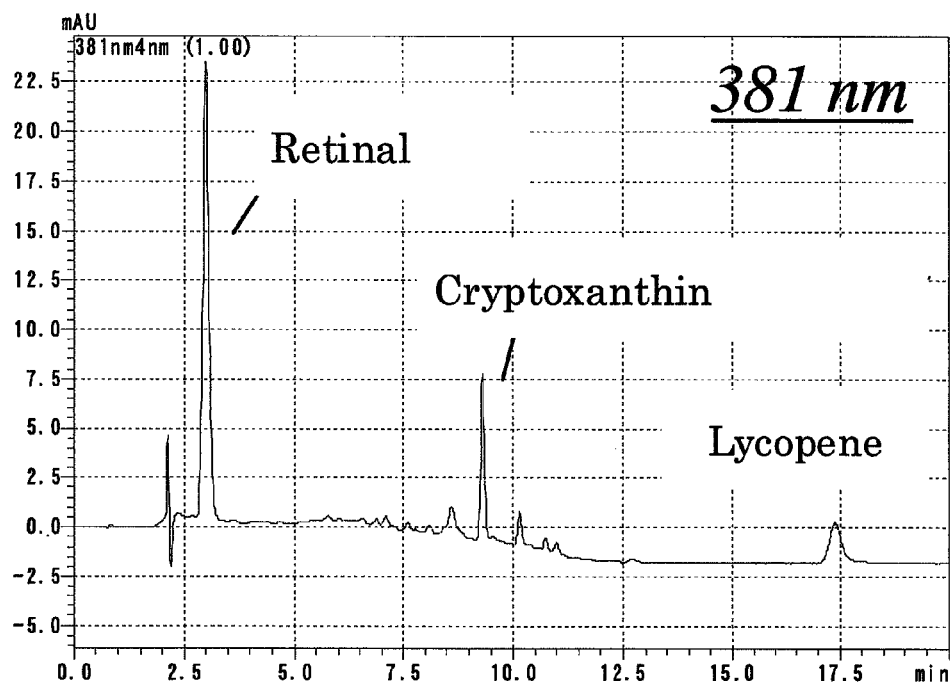
FIG. 2 shows HPLC chromatograms of β-cryptoxanthin, retinal and lycopene at detection wavelengths of 381 nm and 451 nm.
Figure 2:
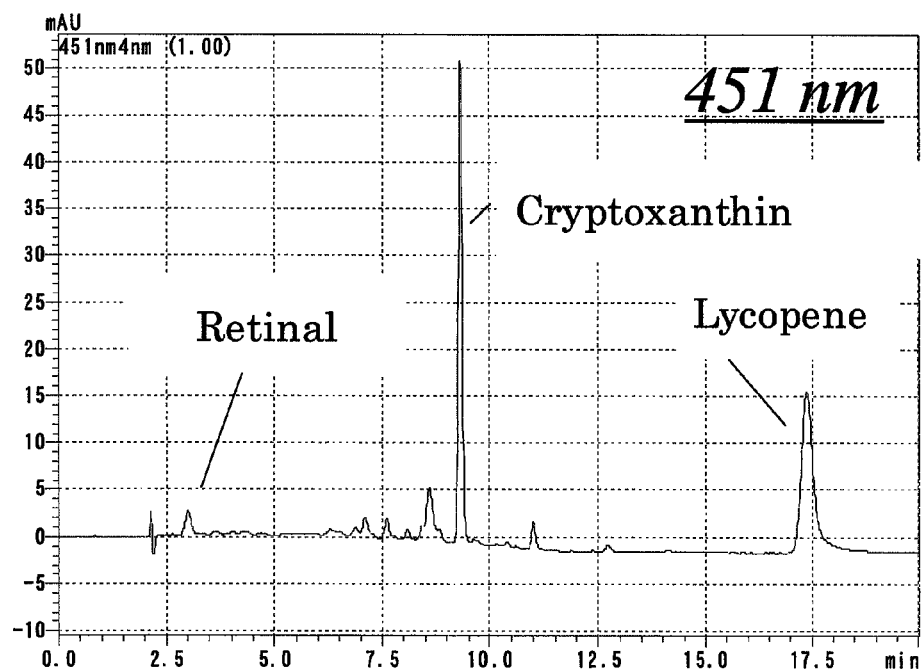

From Table 1 it is understood that deviations tended to be smaller in the case of using retinal as an internal standard than in the case of using lycopene as an internal standard. As to a reason for this tendency, it is inferred that since the peak of lycopene is broader than the peak of retinal, an error tends to be produced in calculation of a peak area more in the case of lycopene than in the case of retinal (chromatograms of the specimen containing retinal, β-cryptoxanthin and lycopene at detection wavelengths of 381 nm and 451 nm are shown in FIG. 2). Further, since the retention time of retinal was shorter than that of lycopene, the measurement time could be reduced.

It was found that measured values tended to higher in the case of using retinal as an internal standard than in the case of using lycopene as an internal standard.

Comparative Example 1

[Effect of Sodium Sulfate]

The procedure of Example 2 was repeated, except that no sodium sulfate was added prior to the saponification reaction, to conduct quantitative analysis of β-cryptoxanthin. The results are shown in Table 2.

TABLE 2

| | Concentration of β-cryptoxanthin (μg/ml) Internal standard: lycopene | Deviation (STDEV) | Concentration of β-cryptoxanthin (μg/ml) Internal standard: retinal | Deviation (STDEV) |
|---|---|---|---|---|
| Sample 1 | 6.72 | 0.24 | 7.06 | 0.31 |
| Sample 2 | 6.61 | 0.62 | 6.74 | 0.47 |
| Sample 3 | 5.56 | 0.31 | 5.65 | 0.08 |
| Sample 4 | 5.95 | 0.55 | 6.34 | 0.71 |
| Sample 5 | 5.28 | 0.15 | 5.56 | 0.14 |
| Sample 6 | 5.31 | 0.26 | 5.55 | 0.30 |

Overall deviations were smaller in the case in which sodium sulfate was added prior to the saponification reaction (Table 1) than in the case in which no sodium sulfate was added prior to the saponification reaction (Table 2). This shows that by adding sodium sulfate at the time of saponification, quantitative determination of β-cryptoxanthin is achieved with good reproducibility.

Example 3

[Study of Saponification Reaction Time]

In accordance with the procedure of quantitative analysis described above, the concentration of β-cryptoxanthin in a Satsuma mandarin juice beverage (7% of concentrated Satsuma mandarin juice) was measured in cases in which the saponification reaction time was 5 minutes, 10 minutes, 30 minutes, 60 minutes and 120 minutes. The results are shown in Table 3.

TABLE 3

|  | Concentration of β-cryptoxanthin (μg/ml) |
|---|---|
| 5 min. | 2.77 |
| 10 min. | 3.61 |
| 30 min. | 4.46 |
| 60 min. | 4.56 |
| 120 min. | 4.55 |

The concentration of β-cryptoxanthin in the case in which the reaction time was 60 minutes was the highest value. This shows that a preferred saponification reaction time is 60 minutes or longer.

The invention claimed is:

1. A method for quantitative analysis of β-cryptoxanthin contained in a sample, comprising:
   mixing the sample with a diethyl ether solution containing an internal standard substance selected from the group consisting of lycopene and retinal,
   wherein the sample is a liquid containing fruit juice or vegetable juice;
   obtaining a diethyl ether layer;
   adding a dehydrating agent to the obtained diethyl ether layer to dehydrate the diethyl ether layer;
   after the dehydration, adding an alkali solution to the dehydrated diethyl ether layer to conduct saponification reaction;
   after the reaction, adding an acid, allowing the mixture to stand still, and then obtaining a diethyl ether layer; and
   subjecting the diethyl ether layer to high-performance liquid chromatography and conducting quantitative analysis of β-cryptoxanthin using an internal standard method.

2. The method of claim 1, wherein the internal standard substance is retinal.

3. The method of claim 1, wherein the dehydrating agent is sodium sulfate.

4. The method of claim 1, wherein the liquid containing fruit juice or vegetable juice is a liquid containing citrus fruit juice.

5. The method of claim 1, wherein the liquid containing fruit juice or vegetable juice is a beverage containing fruit juice.

6. The method of claim 1, wherein the saponification reaction is conducted at 5 to 60° C. in a dark place for 1 to 3 hours.

7. A method for quantitative analysis of β-cryptoxanthin contained in a sample, comprising:
   mixing the sample with a diethyl ether solution containing an internal standard substance, wherein the sample is a liquid containing fruit juice or vegetable juice;
   obtaining a diethyl ether layer;
   adding a dehydrating agent to the obtained diethyl ether layer to dehydrate the diethyl ether layer;
   after the dehydration, adding an alkali solution to the dehydrated ether layer to conduct saponification reaction;
   after the reaction, adding an acid, allowing the mixture to stand still, and then obtaining a diethyl ether layer; and
   subjecting the diethyl ether layer to high-performance liquid chromatography and conducting quantitative analysis of β-cryptoxanthin using an internal standard method.

8. The method of claim 7, wherein the internal standard substance is selected from the group consisting of lycopene, retinal, retinol, dehydroretinol, α-carotene, β-carotene, 13-carotene, capsaicin, astaxanthin and fucoxanthin.

9. The method of claim 8, wherein the internal standard substance is lycopene or retinal.

10. The method of claim 9, wherein the internal standard substance is retinal.

11. A method for quantitative analysis of β-cryptoxanthin contained in a sample, comprising:
   mixing the sample with a diethyl ether solution containing an internal standard substance, wherein the sample is a liquid containing fruit juice or vegetable juice;
   obtaining a diethyl ether layer;
   adding a dehydrating agent to the obtained diethyl ether layer to dehydrate the diethyl ether layer;
   after the dehydration, adding an alkali solution to the dehydrated ether layer to conduct saponification reaction, wherein a volume of the dehydrated ether layer subjected to the saponification reaction is 1 to 3 ml;
   after the reaction, adding an acid, allowing the mixture to stand still, and then obtaining a diethyl ether layer; and
   subjecting the diethyl ether layer to high-performance liquid chromatography and conducting quantitative analysis of β-cryptoxanthin using an internal standard method.

* * * * *